United States Patent [19]

Krempl et al.

[11] Patent Number: 4,525,627
[45] Date of Patent: Jun. 25, 1985

[54] METHOD AND DEVICE FOR CONTINUOUS MEASUREMENT OF THE MASS OF AEROSOL PARTICLES IN GASEOUS SAMPLES

[75] Inventors: Peter W. Krempl; Wolfgang Schindler, both of Graz, Austria

[73] Assignee: A V L Gesellschaft für Verbrennungskraftmaschinen und Messtechnik m.b.H., Graz, Austria

[21] Appl. No.: 491,553

[22] Filed: May 4, 1983

[30] Foreign Application Priority Data

May 6, 1982 [AT] Austria ................ 1788/82

[51] Int. Cl.$^3$ .................. G01J 3/42; G01N 21/21; G01N 21/59
[52] U.S. Cl. .................. 250/345; 250/339; 250/343; 250/340
[58] Field of Search ............ 250/345, 343, 340, 339; 356/438

[56] References Cited

U.S. PATENT DOCUMENTS

| | | | |
|---|---|---|---|
| 2,500,213 | 3/1950 | Stevens | 250/255 |
| 3,973,848 | 8/1976 | Jowett et al. | 356/51 |
| 4,207,469 | 6/1980 | Hopkins et al. | 250/343 |
| 4,229,653 | 10/1980 | Uthe | 250/339 |
| 4,247,773 | 1/1981 | Nexo et al. | 250/339 |

Primary Examiner—Alfred E. Smith
Assistant Examiner—Constantine Hannaher
Attorney, Agent, or Firm—Watson, Cole Grindle & Watson

[57] ABSTRACT

A gaseous sample and a reference volume are traversed by electromagnetic radiation and the absorption caused by the sample, as given by the difference between the radiation intensities after passage through the sample and the reference volume, is measured and used as a measurement value.

By means of radiation of a wavelength in the range between 3.8 and 4.15 μm, the specific mass of particles characterized by broadband absorption—especially graphitic particles—is determined; by means of radiation of a frequency band centered in the wavelength range of 3.35 to 3.5 μm, whose 3 dB bandwidth does not exceed 0.3 μm, the specific total mass of aerosol particles is determined, and by the additional measurement of the resonance absorption at a wavelength in the range of 3.35 to 3.5 μm the percentages of both graphitic and organically soluble particles are determined separately.

In a device for the implementation of the method a beam splitter transmits the radiation of a common radiation source to the sample and the reference volume; by means of a deflection unit the partial beams are reunited and transmitted to an evaluation unit in front of a common detector. With the aid of two transparent plates with parallel faces which are inclined against the incident beam at the Brewster angle, and are inserted in the beam splitter and in the deflection unit, the partial beams are polarized differently; as selector unit a rotatable polarization analyzer is used.

8 Claims, 2 Drawing Figures

METHOD AND DEVICE FOR CONTINUOUS MEASUREMENT OF THE MASS OF AEROSOL PARTICLES IN GASEOUS SAMPLES

BACKGROUND OF THE INVENTION

The present invention relates to a method for the continuous measurement of the mass of aerosol particles in gaseous samples, above all in the exhaust of internal combustion engines, in which the sample is traversed by electromagnetic radiation in the optical Rayleigh range, and in which the absorption caused is measured and is used as a measurement value, and to a device for the implementation of the method.

DESCRIPTION OF THE PRIOR ART

For the continuous measurement of the mass of aerosol particles in gaseous samples methods are known in which the sample loaded with the particles is traversed by a light beam and in which the absorption or scattering caused by the particles is measured. In one of the known methods the radiation wavelengths used are of the same order of magnitude as the radii of the particles; the measurement is taken in the so-called optical Mie range. In this range the absorption coefficient per mass and thus the overall absorption measured strongly depends on the particle size; for this reason the total mass of aerosol particles cannot be determined without determining at least the mean particle size at the same time. As regards the measurement of aerosol particles in the exhaust of internal combustion engines, it is known for instance that the mean particle size will depend on the fuel used, or rather on its additives, and on the operational state of the engine. For this reason a measurement employing this known method will only permit a rough estimate of the total mass of aerosol particles actually emitted.

In another one of the known methods radiation of a greater wavelength is used, e.g., in the infrared range. With these wavelengths, the absorption coefficient per mass is independent of the particle size; the measurement is taken in the so called optical Rayleigh range. Since, however, the absorption cross-section of aerosol particles will decrease considerably with the increasing wavelength of the incident radiation, the accuracy obtained with the very small measurement signal will sharply decline due to the influence of external factors in this known method.

For this reason special measuring techniques have become known for differentiating between changes in the measured absorption due to actual variations in particle emission and changes due to fluctuations having their origin in the equipment, e.g., fluctuations in the intensity of the radiation source. For a precise measurement of the very low absorption taking place when particle concentrations are low—of the order of a few mg/m$^3$—methods are known in which radiation of the same intensity and frequency, preferably derived from the same source, is passed through both a test volume containing the sample and a reference volume; the two volumes must contain the same gas, however, as in the frequency range used radiation is absorbed not only by the particles of the sample proper but also by the components of the carrier gas. In general, these components will absorb only in defined resonance absorption bands which are very dense in the medium and far infrared range, however, i.e., at wavelengths greater than 2 μm. For this reason the known methods of measurement require that the sample particles be filtered out after the absorption of the particle-charged gaseous sample has been determined, and that another absorption measurement be performed with the carrier gas alone. A measurement utilizing the total flow in the exhaust line is therefore not possible; measurements may utilize sample flows only, which is more costly and will yield less reliable test results.

SUMMARY OF THE INVENTION

It is an object of the present invention to avoid the above disadvantages of the known methods and to improve a method of the aforementioned type and a device for the implementation thereof such as to permit in a simple manner measurements of the particle content of gaseous samples even at very low concentrations.

According to the invention this is achieved by the use of electromagnetic radiation of a wavelength in the range between 3.8 and 4.15 μm, the electromagnetic radiation traversing a reference volume in addition to the test volume containing the sample, and by using the difference in the radiation intensities after passage of the two volumes as a measurement value proportional to the specific mass of—mainly graphitic—particles characterized by broadband absorption which are contained in the sample.

The invention is thus based on the accidentally found fact that in the infrared range, or rather in the optical Rayleigh range, there are frequency ranges for the aerosol particles to be measured within which none of the gases contained in the carrier gas, e.g., in the exhaust of internal combustion engines, contributes to the absorption to be measured, so that the absorption of radiation in these frequency ranges is entirely due to the condensed combustion products.

As has been mentioned before, the absorption coefficient of the aerosol particles in this frequency range is very small; this necessitates special measurement set-ups which will permit particle concentrations in the very low ranges (down to a few mg/m$^3$) to be measured sufficiently accurately. This is made possible in a simple manner by passing radiation simultaneously through the test volume containing the sample and through the reference volume, and by absorbing the difference in radiation intensities after the two volumes have been traversed. In view of the above comments concerning the independence of the absorption observed in this frequency range of the composition of the carrier gas, the gas mixture in the reference volume need only be free of aerosol particles. The reference volume may thus contain ordinary air or another gas mixture of similar purity, which will eliminate the need for expensive filtering of the particle-charged sample gas prior to the reference measurement.

A modification of the above method described by the present invention utilizing electromagnetic radiation of a frequency band whose center is in the wavelength range of 3.35 to 3.5 μm and whose 3 dB bandwidth (half width) does not exceed 0.3 μm, has produced the surprising result that the difference in radiation intensities after passage of the two volumes may be directly used as the measurement value which is proportional to the specific total mass of aerosol particles contained in the sample. In addition to the above range of wavelength within which the obtained absorption can be attributed to the graphitic particles mainly, another range of wavelengths may be selected for the electromagnetic radiation in which the obtained absorption may be attributed unambiguously to the condensed combustion products in the exhaust sample.

Another variant of the abovementioned method according to the present invention provides that for the separate determination of the graphitic and organically soluble portions of the aerosol particles the resonance absorption of the organically soluble particles should be measured additionally in the range of 3.35 to 3.5 μm. In the exhaust gas of internal combustion engines these organically soluble components are condensed hydrocarbon droplets mainly. A measurement of the load of the gaseous samples due to these particles at or near the resonance frequency can only be performed if the absorption background due to the broadband graphitic absorption is known, which is of course present in this range. Since the graphitic aerosol particles will absorb according to Rayleigh's laws in the wavelength range used, measuring at a given frequency will permit determination of the absorption over the entire range of validity of these laws, especially at the site of the resonance absorption of interest. In this way the values obtained for the absorption in the wavelength range between 3.35 and 3.5 μm will permit conclusions as to the absorption and thus the mass load of the gaseous sample due to those particles causing the resonance absorption.

In a device for the implementation of the method described by the present invention, in which a beam splitter is positioned in the radiation path behind a radiation source and in front of the test chambers containing the test volume and the reference volume, and in which the partial beams are reunited via a deflection device after having passed the respective test chamber, and in which a selector unit is provided opening with a given periodicity the passage to a detector positioned in the radiation path for one of the two partial beams at a time, provisions are made that the beam splitter as well as the deflection device be furnished with a plane-parallel plate which is transparent for the radiation used and whose surface is inclined against the incident beam at the Brewster angle, and that the selector unit be furnished with a rotatable polarization analyzer located in front of the detector which should transmit only the suitable polarized parts of the united partial beams in accordance with its rotational position.

Positioning the plane-parallel plate at the Brewster angle relative to the incident beam will ensure that only n-polarized parts of the beam are reflected while the p-polarized parts are fully transmitted. Thus test volume and reference volume may be traversed by partial beams which may be identified unambiguously by their different polarization and which may also be passed to the detector separately via the rotating polarization analyzer located in front of the detector, for a determination of their intensity. An alternating signal is received whose period corresponds to that of the analyzer and whose amplitude serves as a measure for the particle content to be determined. This arrangement is characterized by the advantage that due to the geometrical conditions of polarization the intensity registered by the detector always is constant over time, provided that the partial beams have the same intensities and that no aerosol particles are contained in the test volume. Maladjustment of the polarizer is virtually impossible, so that fluctuations in the intensity of the incident radiation will not affect the measurement.

Other designs might include a rotating perforated disk whose apertures are spaced such that the partial beams arrive at the detector alternately, with a given periodicity. A precise machining and careful adjustment of the disk is essential in order to ensure that at no time either the full intensity of both partial beams or none of the partial beams reach the detector, i.e., there should not be any bright or dark peaks at the detector.

In another proposal of the invention a device for implementing the method according to the invention, comprising a beam-splitter located in the radiation path behind a radiation source and in front of the test chambers containing the test volume and the reference volume, is characterized by the addition of two separate detectors which are positioned in the radiation path behind the test and reference volumes, respectively, and by connecting the two detectors with an evaluation unit preferably registering the difference between the signals of the two detectors only. These separate detectors are furnished with electronic circuitry in such a way that the resulting signal is uniquely correlated with the radiation absorption in the gaseous sample and has a known value—preferably zero—if the sample contains no particles.

DESCRIPTION OF THE DRAWING

Following is a more detailed description of the invention as illustrated by the enclosed drawing, wherein.

DESCRIPTION OF THE PREFERRED EMBODIMENTS

Figure 1:
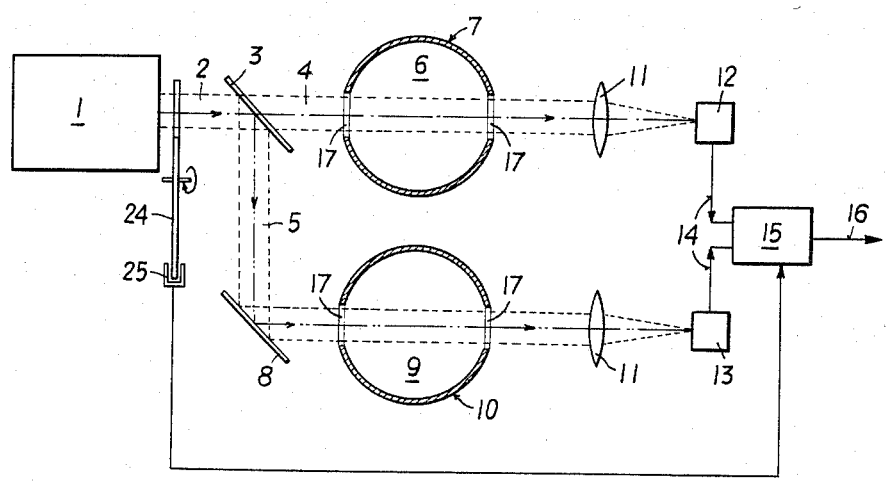
FIG. 1 is a schematic view of a device for the implementation of the method described under the present invention.

The device presented in FIG. 1 serves for the continuous measurement of the mass of aerosol particles in the exhaust of internal combustion engines. A radiation source 1 is provided for the emission of electromagnetic radiation in the infrared range. In the radiation path 2 behind the radiation source 1 a semitransparent mirror 3 is positioned which produces two partial beams 4, 5, one of which (4) passes through a test chamber 7 containing the test volume 6, and the other one (5) through a reference volume 9 in a test chamber 10 after having been deflected by a mirror 8. In the path of the partial beams 4, 5 a focusing lens 11 is located behind each of the two volumes 6 and 9, which will focus the partial beams 4,5 on a separate detector 12, 13. Via lines 14 an evaluation unit 15 is connected to the detectors 12, 13, which preferably will register only the difference between the signals of the two detectors and will transmit it as a measurement signal to the output 16 for further processing.

For the performance of a suitable measurement the exhaust of an internal combustion engine whose mass of absorbing aerosol particles is to be determined, may be directly passed through the test volume 6. The reference volume 9 may be filled with ordinary air or another gas mixture of similar purity for this purpose.

The partial beams 4, 5 passing through the windows 17 of the test chambers 7, 10, which are transparent for the radiation used, are attenuated in correspondence with the respective absorption properties of the gases or gaseous samples contained in the test volume 6 or in the reference volume 9, the difference signal obtained from the evaluation unit 15, or rather its output 16, directly corresponding to the particle charge of the exhaust gas contained in the test volume 6, provided that the radiation parameters have been suitably selected. In this way the set-up presented in this drawing may be used after proper adjustment for determining the specific mass of—mainly graphitic—particles characterized by broadband absorption, for instance with the use of a radiation source 1 whose emitted radiation has a wavelength in the range between 3.8 and 4.15 μm. In this context it should be noted that it will make no difference for the set-up described by the present invention whether a narrow-band radiation source is used or whether the desired frequency is selected by filters in the radiation path 2 or after passing the test and reference volumes. It should further be noted that the difference signal obtained from the evaluation unit 15 should have a well-known constant value, preferably 0, if the exhaust in test volume 6 is free of aerosol particles; for this purpose either the detectors should be adjustable with regard to their sensitivity or it should be possible to insert an attenuator (not shown in this drawing) into one of the two partial beams. In the case of a particle-free test volume 6 and a correct adjustment of the device the difference signal should be constant (preferably zero), even if the intensity of the radiation source has been altered, in particular if the source has been switched off. Infrared detectors incorporating the required facilities for sensitivity adjustment are state of the art.

The difference signal may be adjusted to the desired value in an advantageous manner by means of an electronic control together with a chopper disk. For this purpose a chopper disk 24 is inserted into the radiation path 2 if the test volume 6 is free of particles, which disk will intermittently interrupt the beams with a known frequency; the sensitivity of the detector 12, 13 and/or of the abovementioned attenuator is adjusted such that—in spite of the periodic variation of the radiation intensity acting on the two detectors—the alternating voltage of this period at the output of the evaluation unit 15 will disappear.

The chopper disk 24 may modulate the radiation emitted by source 1 with a preset periodicity even during the measurement proper. As can be seen from the above paragraph the signal from the evaluation unit 15 will oscillate with this periodicity between zero (when the radiation source is covered by the chopper disk) and a value proportional to the mass of aerosol particles in the test volume 6. This A.C. signal may be traced by state-of-the-art "lock-in" devices even if a noise signal of greater intensity is interfering.

The rotatable chopper disk 24 has regularly spaced notches around its circumference which will feed clock signals to the evaluation unit 15 configured as a lock-in amplifier via a pulse generator 25, e.g., of the type of a light-barrier. Only detector signals oscillating with the same periodicity as the signals of the pulse generator 25 are used as measurement signals, which will permit precise measurements even if the background noise is high.

If electromagnetic radiation of a frequency band centered in the wavelength range of 3.35 to 3.5 μm whose 3 dB bandwidth (half width) does not exceed 0.3 μm, arrives at the detectors 12, 13, the difference in the radiation intensities after passage of the two volumes may be directly used as a measurement value proportional to the specific total mass of aerosol particles contained in the sample. Provided that the resonance absorption also is measured in the range of 3.35 to 3.5 μm in addition to the measurement in the former frequency band (3.8 to 4.15 μm)—either in temporal sequence or in another receiver unit (11-16)—this type of arrangement will permit the separate determination of graphitic and non-graphitic or organically soluble portions of aerosol particles, which is of great importance for determining the effects of changes in various engine parameters in the development of new engines and combustion methods.

Figure 2:
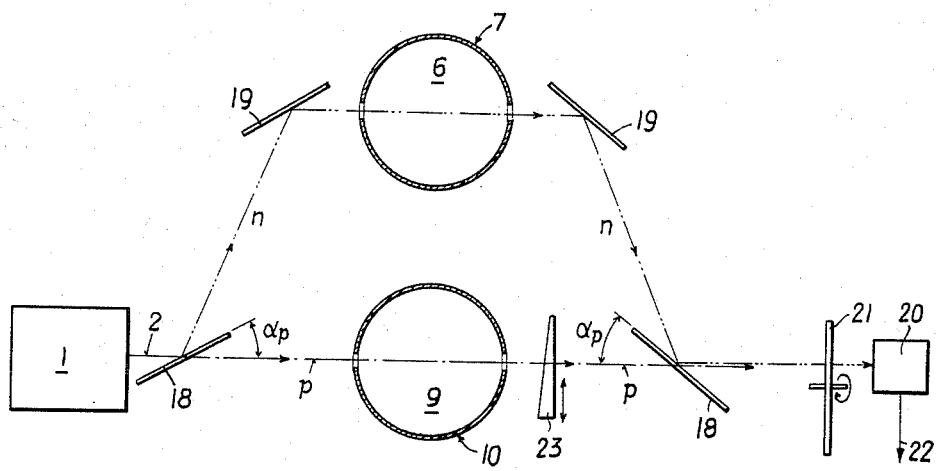
FIG. 2 is a schematic view of another embodiment of the invention.

The device for the continuous measurement of the mass of aerosol particles in gaseous samples presented in FIG. 2 differs from that in FIG. 1 only in that the radiation emitted from the radiation source 1 along the radiation path 2 will first of all arrive at a plate with parallel faces 18 which is transparent for the specific radiation used and whose surface is inclined against the incident beam at the Brewster angle $\alpha_p$, thereby providing a beam splitter producing in a simple manner partial beams which are polarized normally to each other. Due to the physical laws of such a plate an n-polarized part of the incident unpolarized radiation (i.e. both the n-polarized part and the p-polarized part normal to the former still have their full 100% intensity) is reflected towards a mirror 19; the p-polarized parts fully pass the plate 18 in the direction of the reference volume 9. The Brewster angle is defined as follows:

$$\alpha_p = \arctan n_o,$$

$n_o$ being the refractive index of the plate 18. The part passing through the plane-parallel plate is not fully polarized but retains parts of the n-polarized radiation. The parts will decrease proportionally to the increase of the refractive index $n_o$, however. For instance, if germanium is used for the plane-parallel plates 18, with a refractive index of $n_o = 4$ for the infrared range given above, the amount of n-polarized radiation after two passages through the plate is reduced to 1%.

After having been deflected by the mirror 19 which itself must have no polarizing properties of course, the n-polarized partial beam reflected at the Brewster angle will pass the test volume 6 in test chamber 7 and is deflected by another mirror 19 towards another plate 18 located in the radiation path of the p-polarized partial beams passing the reference volume 9 in test chamber 10. This second plate 18 again is inclined against the partial beam at the Brewster angle $\alpha_p$, which will again entail a reflection of the n-polarized parts and a passage of the p-polarized parts. For the sake of greater clarity the partial beams which are reunited behind the second plate 18, are presented side by side in FIG. 2.

In front of a detector 20 a rotatable polarization analyzer 21 is positioned which—in correspondence with its rotational position—will only admit those parts of the united partial beams which are suitably polarized and which are thus registered at the detector 20 in temporal sequence. At the output 22 of the detector 20 an alternating signal is obtained whose period is identical to that of the analyzer 21 and whose amplitude corresponds to the difference in the intensity of the partial beams. The relative intensity of the two partial beams is adjusted via an attenuator 23 such that the detector will deliver a difference signal of zero if the test volume 6 is free of particles.

Infrared sources and detectors of a known type may have fluctuations in intensity and sensitivity which may lead to measurement errors over prolonged measurement cycles. Such errors may be prevented, e.g., by continually calibrating the device by means of a standardized absorber disk. For this purpose an absorber with given absorption characteristics is inserted into the test or reference volume, the insertion period being an integral multiple R of the period of the analyzer 21 (absorber not shown in this drawing).

The difference between measurement values with or without the use of the above absorber will yield the momentarily valid product of source intensity times detector sensitivity with which the measurement value without an absorber may be calibrated. Whereas this set-up will reduce the time resolution of the device by a factor R, the measurement accuracy will be improved considerably.

Instead of the arrangement shown in this drawing for the polarization of the two partial beams, conventional polarizers could also be used in the radiation path, which would be more expensive, however, and would raise the cost of the entire device considerably.

We claim:

1. A method for the continuous measurement of the mass of aerosol particles in a gaseous sample, preferably in the exhaust of an internal combustion engine, the sample being traversed by electromagnetic radiation in the optical Rayleigh range and the absorption caused being measured and utilized as a measurement value, wherein electromagnetic radiation of a wavelength in the range between 3.8 and 4.15 $\mu$m is used, said radiation traversing a reference volume in addition to a test volume containing said sample, and the difference in the radiation intensities after passage of said two volumes is used as a measurement value proportional to the specific mass of—mainly graphitic—particles characterized by broadband absorption which are contained in said sample.

2. A method as in claim 1, wherein for the separate determination of the graphitic and organically soluble portions of the aerosol particles the resonance absorption of the organically soluble particles is measured additionally at a wavelength in the range of 3.35 to 3.5 $\mu$m.

3. A device for the continuous measurement of the mass of aerosol particles in a gaseous sample, preferably in the exhaust of an internal combustion engine, the sample being traversed by electromagnetic radiation in the optical Rayleigh range and the absorption caused being measured and utilized as a measurement value, wherein electromagnetic radiation of a wavelength in the range between 3.8 and 4.15 $\mu$m is used, said radiation traversing a reference volume in addition to a test volume containing said sample, and the difference in the radiation intensities after passage of said two volumes is used as a measurement value proportional to the specific mass of—mainly graphitic—particles characterized by broadband absorption which are contained in said sample, comprising a radiation source for said electromagnetic radiation, two test chambers containing a test volume and a reference volume, a beam splitter positioned in the radiation path behind said radiation source and in front of said test chamber for producing two separated partial beams, a deflection device, said partial beams being reunited via said deflection device after having passed the respective test chamber, a detector, a selector unit which is opening with a given periodicity the beam passage to said detector positioned in the radiation path for one of said two partial beams at a time, said beam splitter as well as said deflection device are provided with a plane-parallel plate which is transparent for the radiation used and whose surface is inclined against the incident beam at the Brewster angle ($\alpha_p$), and said selector unit is provided with a rotating polarization analyzer located in front of said detector, which transmits only the suitably polarized parts of the united partial beams in accordance with its rotational position.

4. A device for the continuous measurement of the mass of aerosol particles in a gaseous sample, preferably in the exhaust of an internal combustion engine, the sample being traversed by electromagnetic radiation in the optical Rayleigh range and the absorption caused being measured and utilized as a measurement value, wherein electromagnetic radiation is used of a frequency band whose center is in the wavelength range of 3.35 to 3.5 $\mu$m and whose 3 dB bandwidth does not exceed 0.3 $\mu$m, said radiation traversing a reference volume in addition to a test volume containing said sample, and the difference in the radiation intensities after passage of said two volumes is used as a measurement value proportional to the specific total mass of aerosol particles contained in said sample, comprising a radiation source for said electromagnetic radiation, two test chambers containing a test volume and a reference volume, a beam splitter positioned in the radiation path behind said radiation source and in front of said test chambers for producing two separated partial beams, a deflection device, said partial beams are reunited via said deflection device after having passed the respective test chamber, a detector, a selector unit which is opening with a given periodicity the beam passage to said detector positioned in the radiation path for one of said two partial beams at a time, said beam splitter as well as said deflection device are provided with a plane-parallel plate which is transparent for the radiation used and whose surface is inclined against the incident beam at the Brewster angle ($\alpha_p$), and said selector unit is provided with a rotating polarization analyzer located in front of said detector, which transmits only the suitably polarized parts of the united partial beams in accordance with its rotational position.

5. A device for the continuous measurement of the mass of aerosol particles in a gaseous sample, preferably in the exhaust of an internal combustion engine, the sample being traversed by electromagnetic radiation in the optical Rayleigh range and the absorption caused being measured and utilized as a measurement value, wherein electromagnetic radiation of a wavelength in the range between 3.8 and 4.15 $\mu$m is used, said radiation traversing a reference volume in addition to a test volume containing said sample, and the difference in the radiation intensities after passage of said two volumes is used as a measurement value proportional to the specific mass of—mainly graphitic—particles characterized by broadband absorption which are contained in said sample, for the separate determination of the graphitic and organically soluble portions of the aerosol particles the resonance absorption of the organically soluble particles is measured additionally at a wavelength in the range of 3.35 to 3.5 $\mu$m, comprising a radiation source for said electromagnetic radiation, two test chambers containing a test volume and a reference volume, a beam splitter positioned in the radiation path behind said radiation source and in front of said test chambers for producing two separated partial beams, a deflection device, said partial beams are reunited via said deflection device after having passed the respective test chamber, a detector, a selector unit which is opening with a periodicity the beam passage to said detector positioned in the radiation path for one of said two partial beams at a time, said beam splitter as well as said deflection device are provided with a plane-parallel plate which is transparent for the radiation used and whose surface is inclined against the incident beam at the Brewster angle ($\alpha_p$), and said selector unit is provided with a rotating polarization analyzer located in front of said detector, which transmits only the suitably polarized parts of the united partial beams in accordance with its rotational position.

6. A device for the continuous measurement of the mass of aerosol particles in a gaseous sample, preferably in the exhaust of an internal combustion engine, the sample being traversed by electromagnetic radiation in the optical Rayleigh range and the absorption caused being measured and utilized as a measurement value, wherein electromagnetic radiation of a wavelength in the range between 3.8 and 4.15 $\mu$m is used, said radiation traversing a reference volume in addition to a test volume containing said sample, and the difference in the radiation intensities after passage of said two volumes is used as a measurement value proportional to the specific mass of—mainly graphitic—particles characterized by broadband absorption which are contained in said sample, comprising a radiation source for said electromagnetic radiation, two test chambers containing a test volume and a reference volume, a beam splitter positioned in the radiation path behind said radiation source and in front of said test chambers for producing two separated partial beams, two separate detectors positioned in the radiation path behind said test chambers, and wherein an evaluation unit is provided, which is connected with said two detectors and registering the difference between the signals of said two detectors only.

7. A device for the continuous measurement of the mass of aerosol particles in a gaseous sample, preferably in the exhaust of an internal combustion engine, the sample being traversed by electromagnetic radiation in the optical Rayleigh range and the absorption caused being measured and utilized as a measurement value, wherein electromagnetic radiation is used of a frequency band whose center is in the wavelength range of 3.35 to 3.5 $\mu$m and whose 3 dB bandwidth does not exceed 0.3 $\mu$m, said radiation traversing a reference volume in addition to a test volume containing said sample, and the difference in the radiation intensities after passage of said two volumes is used as a measurement value proportional to the specific total mass of aerosol particles contained in said sample, comprising a radiation source for said electromagnetic radiation, two test chambers containing a test volume and a reference volume, a beam splitter positioned in the radiation path behind said radiation source and in front of said test chambers for producing two separated partial beams, two separate detectors positioned in the radiation path behind said test chambers, and wherein an evaluation unit is provided, which is connected with said two detectors and registering the difference between the signals of said two detectors only.

8. A device for the continuous measurement of the mass of aerosol particles in a gaseous sample, preferably in the exhaust of an internal combustion engine, the sample being traversed by electromagnetic radiation in the optical Rayleigh range and the absorption caused being measured and utilized as a measurement value, wherein electromagnetic radiation of a wavelength in the range between 3.8 and 4.15 $\mu$m is used, said radiation traversing a reference volume in addition to a test volume containing said sample, and the difference in the radiation intensities after passage of said two volumes is used as a measurement value proportional to the specific mass of—mainly graphitic—particles characterized by broadband absorption which are contained in said sample, for the separate determination of the graphitic and organically soluble portions of the aerosol particles the resonance absorption of the organically soluble particles is measured additionally at a wavelength in the range of 3.35 to 3.5 $\mu$m, comprising a radiation source for said electromagnetic radiation, two test chambers containing a test volume and a reference volume, a beam splitter positioned in the radiation path behind said radiation source and in front of said test chambers for producing two separated partial beams, two separate detectors positioned in the radiation path behind said test chambers, and wherein an evaluation unit is provided, which is connected with said two detectors and registering the difference between the signals of said two detectors only.

* * * * *

UNITED STATES PATENT OFFICE
CERTIFICATE OF CORRECTION

PATENT NO. : 4,525,627
DATED : June 25, 1985
INVENTOR(S) : Krempl et al

It is certified that error appears in the above-identified patent and that said Letters Patent are hereby corrected as shown below:

On the title page;

--(73) Assignee: A V L Gesellschaft für Verbrennungskraftmaschinen und Messtechnik M.B.H., Prof. Dr. Dr. h.c. Hans List, an Austrian Corporation--.

Signed and Sealed this

First Day of October 1985

[SEAL]

Attest:

Attesting Officer

DONALD J. QUIGG

Commissioner of Patents and Trademarks—Designate